United States Patent [19]
Mosby

[11] Patent Number: 4,905,269
[45] Date of Patent: Feb. 27, 1990

[54] CONTOURED CASSETTE

[76] Inventor: Richard A. Mosby, P.O. Box 20554, Houston, Tex. 77225

[21] Appl. No.: 155,708

[22] Filed: Feb. 16, 1988

[51] Int. Cl.$^4$ .......................... G03B 42/04; A61B 6/04
[52] U.S. Cl. ...................................... 378/182; 378/37; 378/167
[58] Field of Search .................. 378/37, 167, 177, 58, 378/182, 180, 178, 181, 169, 59, 184, 185, 208; 206/455

[56] References Cited

U.S. PATENT DOCUMENTS

| | | | |
|---|---|---|---|
| 3,851,178 | 11/1974 | Borden | 378/169 |
| 3,963,933 | 6/1976 | Henkes, Jr. | 378/37 |
| 3,973,126 | 8/1976 | Redington et al. | 378/37 |
| 4,090,084 | 5/1978 | Epstein et al. | 378/37 |
| 4,563,768 | 1/1986 | Read et al. | 378/37 |
| 4,691,333 | 9/1987 | Gabreile et al. | 378/37 |

FOREIGN PATENT DOCUMENTS

| | | | |
|---|---|---|---|
| 2610111 | 9/1977 | Fed. Rep. of Germany | 378/37 |
| 2141910 | 1/1985 | United Kingdom | 378/180 |

Primary Examiner—Carolyn E. Fields
Assistant Examiner—Joseph A. Hynds
Attorney, Agent, or Firm—Neal J. Mosely

[57] ABSTRACT

An energy detecting cassette for detection of electromagnetic energy (X-ray, magnetic resonance imaging (MRI), etc), sound energy, and other detectable forms of energy used for examination of the interior of objects consists of a flat box for holding an image fixing medium having an edge wall portion contoured to fit the surface of an object adjacent or next to the portion of the object to be subjected to detectable energy.

5 Claims, 2 Drawing Sheets

CONTOURED CASSETTE

BACKGROUND OF THE INVENTION

1. Field of the Invention

This invention relates to energy detecting cassettes for detection of electromagnetic energy (X-ray, magnetic resonance imaging (MRI), etc), sound energy, and other detectable forms of energy used for examination of the interior of objects, and more particularly to cassettes having an edge wall portion contoured to fit the surface of an object adjacent or next to the portion of the object to be subjected to detectable energy.

2. Brief Description of the Prior Art

Cassettes have long been used in energy detecting devices for detection of X-ray and other detectable forms of energy used for examination of the interior of objects. Such cassettes are flat boxes which hold an image fixing medium (X-ray film or the like) in a position adjacent the portion of the object or body being subjected to detection or scanning. Cassettes are usually made of plastic or cardboard. Metal cassettes may be used where the metal does not interfere with the image being detected or fixed.

Standard detection or imaging cassettes are thin, flat, rectangular (or square) plastic or cardboard boxes which hold the film or other energy detecting medium. The flat edge wall of conventional square or rectangular cassettes often does not conform to the subject or structure outline which limits the subject evaluation or measurement.

In mammography, the standard cassettes used are square or rectangular. This configuration precludes consistent evaluation of deep breast tissue and therefore deep lesions or cancers may go undetected. In industrial uses, the standard cassettes used are likewise square or rectangular which may not conform to the subject or adjacent structure outline.

SUMMARY OF THE INVENTION

It is therefore an object of the present invention to provide a new and improved cassette for detection of electromagnetic energy (X-ray, magnetic resonance imaging (MRI), etc), sound energy, and other detectable forms of energy used for examination of the interior of objects.

It is another object of this invention to provide a new and improved cassette for detection of electromagnetic energy (X-ray, magnetic resonance imaging (MRI), etc), sound energy, and other detectable forms of energy used for examination of the interior of objects having an edge wall portion contoured to fit the surface of an object adjacent to the portion of the object to be subjected to detectable energy.

Another object of this invention is to provide a new and improved cassette for detection of electromagnetic energy (X-ray, magnetic resonance imaging (MRI), etc), sound energy, and other detectable forms of energy used for examination of the interior of the human body which increases the comfort of examination.

Another object of this invention is to provide a new and improved cassette for detection of electromagnetic energy (X-ray, magnetic resonance imaging (MRI), etc), sound energy, and other detectable forms of energy used for examination of the interior of objects configured to evaluate portions of the body which are substantially inaccessible.

Other objects of the invention will become apparent from time to time throughout the specification and claims as hereinafter related.

The above noted objects and other objects of the invention are accomplished by a novel cassette for detection of electromagnetic energy (X-ray, magnetic resonance imaging (MRI), etc), sound energy, and other detectable forms of energy used for examination of the interior of objects having an edge wall portion contoured to fit the surface of an object adjacent to the portion of the object to be subjected to detectable energy. In use, the cassette is placed adjacent the portion of the object to be recorded or imaged with the contoured edge wall fitting the surface and permitting energy from a source of detectable energy to reach the recording or imaging medium with a minmum of interference. This cassette maximizes comfort in use and efficiency of recording or imaging and avoids the necessity of using special energy sources for recording or imaging body portions which are relatively inaccessible.

DESCRIPTION OF THE PREFERRED EMBODIMENTS

In the various views an energy detecting cassette is shown for detection of electromagnetic energy (X-ray, magnetic resonance imaging (MRI), etc), sound energy, and other detectable forms of energy used for examination of the interior of objects consists of a box for holding an image fixing medium having an edge wall portion contoured to fit the surface of an object adjacent to the portion of the object to be subjected to detectable energy. The cassette is constructed of cardboard, plastic, metal and/or other durable materials having properties which permit the transfer of energy to the detection material (film) or device (sonic, magnetic resonance imaging (MRI), etc.) for detection. The cassette has one or more edge walls arced in a manner that allows it to fit or contour to an adjacent structure or a structure to be evaluated. This contouring enhances and increases the amount of information derived from the electromagnetic energy (X-ray, magnetic resonance imaging (MRI), etc), sound energy, and other detectable forms of energy used for detection, recording and/or enhancing.

Figure 4:
FIG. 4 is an edge elevation of the cassettes shown in FIGS. 1-3.
Figure 1:
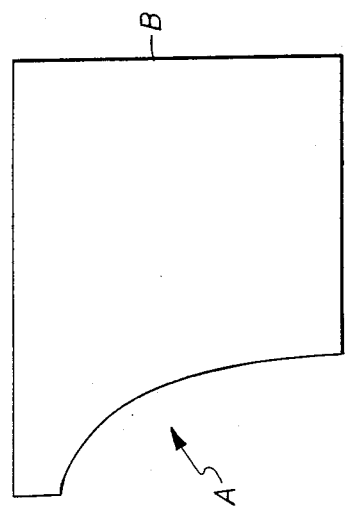
FIG. 1 is a plan view of an energy detecting cassette for detection of electromagnetic energy (X-ray, magnetic resonance imaging (MRI), etc), sound energy, and other detectable forms of energy used for examination of the interior of objects consisting of a box for holding an image fixing medium having an edge wall portion contoured to fit the surface of a female or male body adjacent to the breast for use in mammography.

In FIG. 1, there is shown an energy detecting cassette B for detection of electromagnetic energy (X-ray, magnetic resonance imaging (MRI), etc), sound energy, and other detectable forms of energy used for examination of the interior of objects consisting of a box for holding an image fixing medium having an edge wall portion A contoured to fit the surface of a female body adjacent to the breast for use in mammography. The thickness of the cassette B and contoured edge wall A are shown in FIG. 4.

Figure 3:
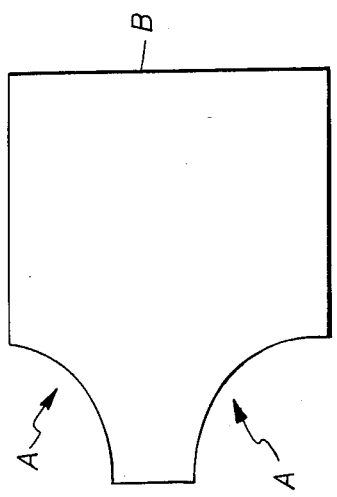
FIG. 3 is a plan view of an energy detecting cassette for detection of electromagnetic energy (X-ray, magnetic resonance imaging (MRI), etc), sound energy, and other detectable forms of energy used for examination of the interior of objects consisting of a box for holding an image fixing medium having an edge wall portion contoured for still another application.
Figure 2:
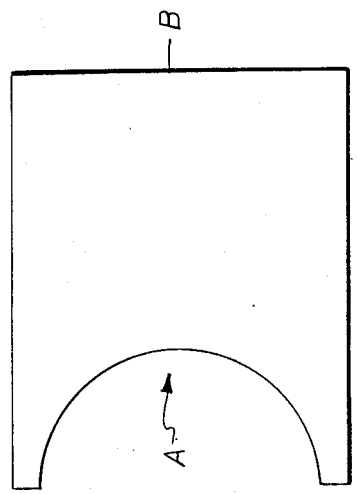
FIG. 2 is a plan view of an energy detecting cassette for detection of electromagnetic energy (X-ray, magnetic resonance imaging (MRI), etc), sound energy, and other detectable forms of energy used for examination of the interior of objects consisting of a box for holding an image fixing medium having an edge wall portion contoured for a different application.

In FIGS. 2 and 3, there are shown energy detecting cassettes B for detection of electromagnetic energy (X-ray, magnetic resonance imaging (MRI), etc), sound energy, and other detectable forms of energy used for examination of the interior of objects consisting of a box for holding an image fixing medium having an edge wall portion or portions A contoured for other appliations requiring a fit against a particular surface. The thickness of the cassette B and contoured edge wall A are shown in FIG. 4.

Figure 5:
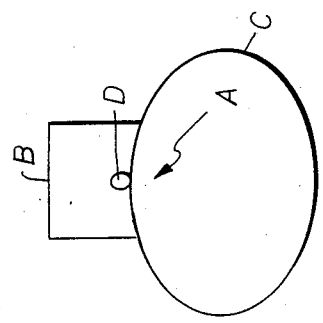
FIG. 5 is a view of an energy detecting cassette for detection of electromagnetic energy (X-ray, magnetic resonance imaging (MRI), etc), sound energy, and other detectable forms of energy used for examination of the interior of objects consisting of a box for holding an image fixing medium having an edge wall portion contoured to fit the stomach and positioned to evaluate an umbilical hernia.

In FIG. 5, there is shown an energy detecting cassette B for detection of electromagnetic energy (X-ray, magnetic resonance imaging (MRI), etc), sound energy, and other detectable forms of energy used for examination of the interior of objects consisting of a box for holding an image fixing medium having an edge wall portion A contoured as in FIG. 1 fitting the stomach wall C and positioned to evaluate an umbilical hernia D.

Figure 6:
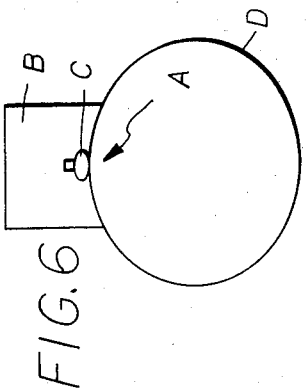
FIG. 6 is a view of an energy detecting cassette for detection of electromagnetic energy (X-ray, magnetic resonance imaging (MRI), etc), sound energy, and other detectable forms of energy used for examination of the interior of objects consisting of a box for holding an image fixing medium having an edge wall portion contoured to fit the wall of a pipe and positioned to evaluate a bolt positioned therein.

In FIG. 6, there is shown an energy detecting cassette B for detection of electromagnetic energy (X-ray, magnetic resonance imaging (MRI), etc), sound energy, and other detectable forms of energy used for examination of the interior of objects consisting of a box for holding an image fixing medium having an edge wall portion A contoured to fit the wall of a pipe D and positioned to evaluate a bolt C positioned adjacent thereto.

Figure 7:
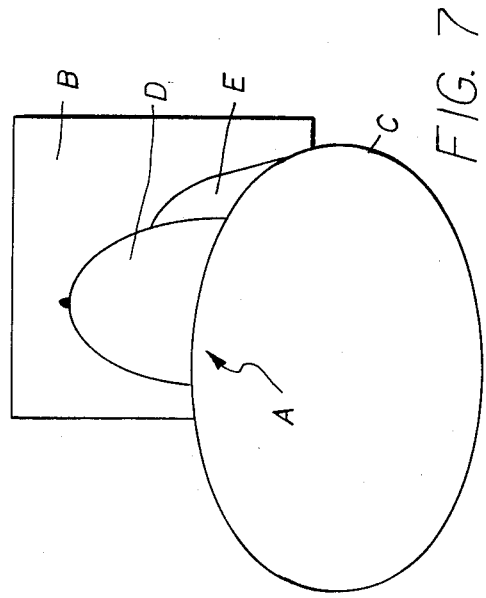
FIG. 7 is a plan view of an energy detecting cassette for detection of electromagnetic energy (X-ray, magnetic resonance imaging (MRI), etc), sound energy, and other detectable forms of energy used for examination of the interior of objects consisting of a box for holding an image fixing medium having an edge wall portion contoured to fit and fitted against a female and male body portion adjacent to the breast.
Figure 8:
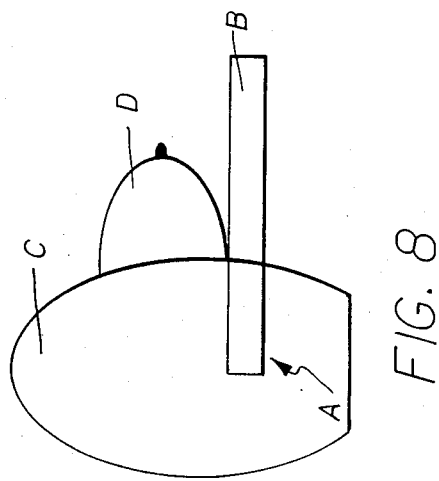
FIG. 8 is a view in side elevation of the cassette, body and breast shown in FIG. 7.

In FIGS. 7 and 8, an energy detecting cassette B for detection of electromagnetic energy (X-ray, magnetic resonance imaging (MRI), etc), sound energy, and other detectable forms of energy used for examination of the interior of objects consists of a box for holding an image fixing medium having an edge wall portion A contoured to fit and fitted against a female or male chest C adjacent to the breast D. This arrangement permits a more thorough examination of the breast D and auxiliary slip E in that deeper breast tissue and auxiliary slip are completely submitted for detection. An X-ray beam presented perpendicularly to the cassette B and the film supported therein allows a more complete examination of these structures. Standard cassettes are geometrical in shape and preclude this detection.

Figure 9:
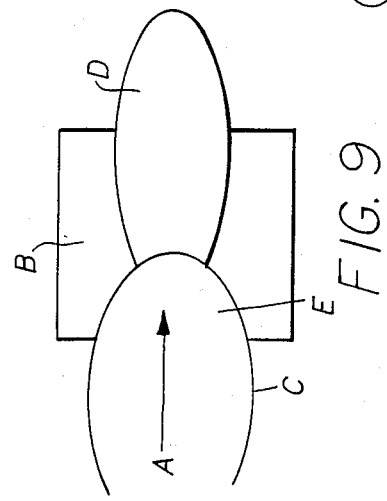
FIG. 9 is a plan view of a cassette contoured to fit the body and positioned to evaluate the should and upper arm.

In FIG. 9, cassette B has surface A contoured to fit the chest C and positioned to evaluate the shoulder E and upper arm D.

Figure 10:
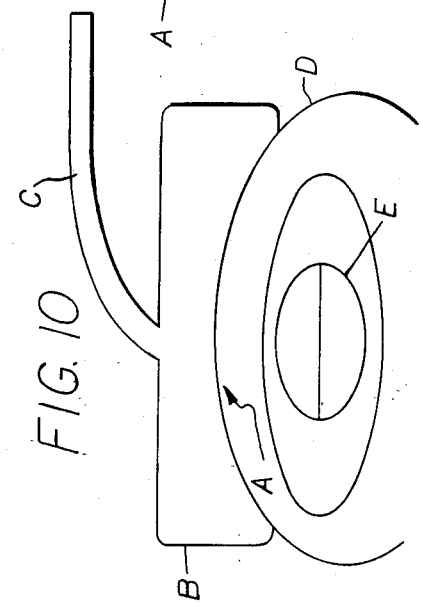
FIG. 10 is a view of an ultrasonic transducer array contoured to fit the body and positioned to evaluate the abdomen of a pregnant female.

In sonography, the energy generator and detector are the same cassette and contouring to fit the surface of the object being scanned or imaged has the same advantage. In FIG. 10, ultrasonic transducer array B' is contoured as at A to fit the abdomen D of a pregnant woman to detect and evaluate pregnancy and the fetus E.

Figure 11:
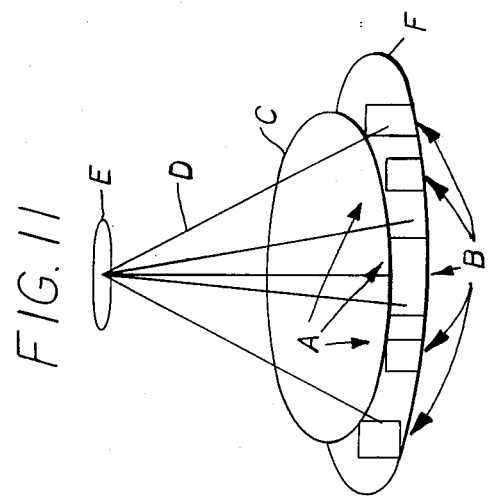
FIG. 11 is a view in side elevation of a detector array for computed tomography.

In computed tomography, the energy generator and detector form a unit which detectors are contoured to fit the surface of the object being scanned or imaged and has the same advantage. In FIG. 11, detector array B" is contoured as at A to fit the chest C. An X-ray tube E emits X-rays D to detector array B" and holder F contoured as at A.

Figure 12:
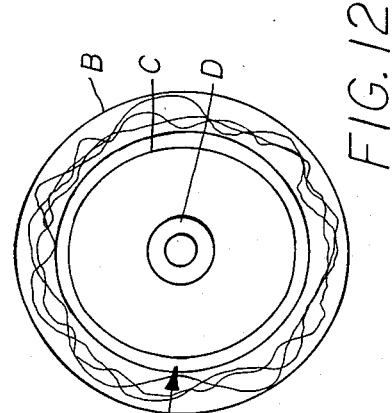
FIG. 12 is side view of a contoured magnet used for magnetic imaging.

In Magnetic Resonance Imaging (MRI), the energy generator and detector are the same. Contouring to fit the surface of the object being scanned or imaged has the same advantage. In FIG. 12, magnet B1 is contoured as at A to fit the thigh C to evaluate the femur D.

While this invention has been shown fully and completely with special emphasis on certain preferred embodiments, it should be understood that within the scope of the appended claims the invention may be practiced otherwise than as specifically described herein.

I claim:

1. An X-ray cassette for examination of the interior of objects, said cassette comprising a flat hollow box for holding an X-ray film, said box being of a material permitting transmission of X-rays to said X-ray film, and said box having an edge wall portion with a concave contour for receiving an X-ray film having the same concave contour and comprising means for receiving X-ray film having the same contour, the contoured edge being configured to fit around the surface of an object adjacent to the portion of the object to be X-rayed to position said X-ray film more closely in line with the X-rays being transmitted thereto.

2. A cassette according to claim 1 in which said box is constructed of cardboard or plastic and said receiving means comprising means openable for insertion of a contoured X-ray film.

3. A cassette according to claim 1 in which said box edge wall portion is contoured to fit against and at least partially around a human body portion so that the cassette may position the edge of an X-ray film in close contact with the body adjacent and around a body part to be X-ray photographed.

4. An X-ray cassette for use in mammography comprising a flat hollow box for holding an X-ray film,
said box being of a material permitting transmission of X-rays to said X-ray film, and
said box having an edge wall portion with a concave contour for receiving an X-ray film having the same concave contour and comprising means for receiving X-ray film having the same contour, the contoured edge being configured to fit around a body surface adjacent to the portion of a breast to be X-rayed to position said X-ray film more closely in line with the X-rays being transmitted thereto.

5. An X-ray cassette containing a film for examination of the interior of objects, said cassette comprising a flat hollow box,
said box being of a material permitting transmission of X-rays to said X-ray film, and
said box having an edge wall portion with a concave contour, said X-ray film having the same concave contour and the contoured cassette edge being configured to fit around the surface of an object adjacent to the portion of the object to be X-rayed to position the contoured edge of said X-rayed film more closely in line with the X-rays being transmitted thereto.

* * * * *